United States Patent
Xiang et al.

(10) Patent No.: US 10,670,529 B2
(45) Date of Patent: Jun. 2, 2020

(54) METHOD FOR DETECTING COAL QUALITY USING RAMAN SPECTROSCOPY

(71) Applicant: HUAZHONG UNIVERSITY OF SCIENCE AND TECHNOLOGY, Wuhan (CN)

(72) Inventors: Jun Xiang, Wuhan (CN); Jun Xu, Wuhan (CN); Sheng Su, Wuhan (CN); Song Hu, Wuhan (CN); Yi Wang, Wuhan (CN); Long Jiang, Wuhan (CN); Mengxia Qing, Wuhan (CN); Zhe Xiong, Wuhan (CN); Hao Tang, Wuhan (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 0 days.

(21) Appl. No.: 16/247,544

(22) Filed: Jan. 14, 2019

(65) Prior Publication Data

US 2019/0154585 A1    May 23, 2019

Related U.S. Application Data (63) Continuation-in-part of application No. PCT/CN2016/112501, filed on Dec. 28, 2016.

(30) Foreign Application Priority Data

Jul. 27, 2016   (CN) .......................... 2016 1 0600182

(51) Int. Cl.
*G01J 3/44*       (2006.01)
*G01N 21/65*   (2006.01)
*G01N 33/22*   (2006.01)

(52) U.S. Cl.
CPC ........... *G01N 21/65* (2013.01); *G01N 33/222* (2013.01)

(58) Field of Classification Search
CPC ......... G01N 21/65; G01N 33/222; G01J 3/44; G01J 3/443

(Continued)

(56) References Cited

U.S. PATENT DOCUMENTS 4,875,771 A * 10/1989 Bowley .................. G01N 21/87
356/30

FOREIGN PATENT DOCUMENTS

| CN | 101949852 A | 1/2011 |
| CN | 102564989 A | 7/2012 |

(Continued)

OTHER PUBLICATIONS

Analysis of coal by diffuse reflectance near-infrared spectroscopy, Andres et al, Analytica Chimica Acta 535 (2005) 123-132 (Year: 2005).*

(Continued)

*Primary Examiner* — Tarifur R Chowdhury
*Assistant Examiner* — Jonathon Cook
(74) *Attorney, Agent, or Firm* — Matthias Scholl P.C.; Matthias Scholl (57) ABSTRACT

A method for detecting coal quality, including: selecting a plurality of standard coals, acquiring Raman spectral characteristic parameters of each standard coal and characteristic parameters of coal quality components of each standard coal, calculating a mapping relationship between the Raman spectral characteristic parameters and the characteristic parameters of the coal quality components of each standard coal, to establish a relational database of the Raman spectral characteristic parameters and the characteristic parameters of the coal quality components; providing coal to be ana- (Continued)

lyzed, conducting Raman spectroscopy on the coal to yield Raman spectrum of the coal, and performing curve-fitting calculation on the Raman spectrum of the coal to obtain Raman spectral characteristic parameters of the coal; and comparing the Raman spectral characteristic parameters of the coal with the Raman spectral characteristic parameters of the relational database.

7 Claims, 6 Drawing Sheets

(58) Field of Classification Search
USPC .......................................................... 356/301
See application file for complete search history.

(56) References Cited

FOREIGN PATENT DOCUMENTS

| CN | 103529012 A | 1/2014 |
|---|---|---|
| CN | 104655583 A | 5/2015 |
| CN | 105223184 A | 1/2016 |
| CN | 106198488 A | 12/2016 |
| JP | 2012122990 A | 6/2012 |
| JP | 2014202711 A | 10/2014 |

OTHER PUBLICATIONS

Application of Infrared Spectroscopy in the Detection of Coal Quality of Power Plant International Conference of Electrical, Automation and Mechanical Engineering (EAME 2015) (Year: 2015).*

Assessing the quality of metallurgical coke by Raman spectroscopy G. Rantitsch et al. / International Journal of Coal Geology 130 (2014) 1-7 (Year: 2014).*

Zhaoxi Zuo et al., Application of Laser Raman Spectroscopy to the Evaluation of the High- and Overhigh-maturity of Shale and Coal, Rock and Mineral Analysis, Mar. 2016, pp. 193-198, vol. 35, No. 2, Rock and Mineral Analysis Publisher, Tianjin, China.

\* cited by examiner

METHOD FOR DETECTING COAL QUALITY USING RAMAN SPECTROSCOPY

CROSS-REFERENCE TO RELATED APPLICATIONS

This application is a continuation-in-part of International Patent Application No. PCT/CN2016/112501 with an international filing date of Dec. 28, 2016, designating the United States, now pending, and further claims foreign priority benefits to Chinese Patent Application No. 201610600182.5 filed Jul. 27, 2016. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The disclosure belongs to the field of coal quality detection, and more specifically relates to a method for detecting coal quality using Raman spectroscopy.

Description of the Related Art

Coal quality refers to the physical and chemical properties of coals. Its main indexes include elemental compositions, ash content, moisture, sulfur content, calorific value, volatiles matter, coking property, and bonding property.

Conventional coal quality analysis is conducted in the laboratory, is complex, and is time-consuming.

Petrographic analysis is a widely-used method for analyzing coal quality. However, the method involves a complex sample preparation process, and the coal quality parameters obtained are incomplete.

Nuclear detection of the coal quality is relatively expensive, and the detection results are often inaccurate.

SUMMARY OF THE INVENTION

In view of the above-described problems, it is an objective of the invention to provide a method for detecting coal quality that can efficiently, accurately, and in one-step acquire characteristic parameters of coals. The method is applicable to the coal quality analysis and on-line detection in coal mining, coal-fired power plants, etc., and is also applicable to the detection of coal quality components in the laboratory research.

To achieve the above objective, according to one embodiment of the invention, there is provided a method for detecting coal quality, the method comprising:

(1) selecting a plurality of standard coals of different coal ranks and different ash contents, acquiring Raman spectral characteristic parameters of each standard coal and characteristic parameters of coal quality components of each standard coal, calculating a mapping relationship between the Raman spectral characteristic parameters and the characteristic parameters of the coal quality components of each standard coal, to establish a relational database of the Raman spectral characteristic parameters and the characteristic parameters of the coal quality components;

(2) providing coal to be analyzed, conducting a Raman spectroscopy on the coal following operations in (1), to yield Raman spectrum of the coal, and performing curve-fitting calculation on the Raman spectrum of the coal, to obtain Raman spectral characteristic parameters of the coal; and (3) comparing the Raman spectral characteristic parameters of the coal with the Raman spectral characteristic parameters of the relational database, and based on the mapping relationship between the Raman spectral characteristic parameters and the characteristic parameters of the coal quality components obtained in 1), determining coal quality of the coal.

In a class of this embodiment, the plurality of standard coals are raw ore coals and each standard coal is a representative coal type.

In a class of this embodiment, the Raman spectra is preprocessed in (1). The preprocessing comprises segmenting the Raman spectra into first-order Raman spectra and second-order Raman spectra, and then removing baselines of the first-order Raman spectra and the second-order Raman spectra.

In a class of this embodiment, a detection range of the Raman spectra is between 600 and 3400 $cm^{-1}$, with 600-2200 $cm^{-1}$ as the first-order Raman spectra and 2200-3400 $cm^{-1}$ as the second-order Raman spectra.

In a class of this embodiment, in (2), a total peak area of the first-order Raman spectra is calculated, and the curve-fitting calculation is conducted on the second-order Raman spectra.

In a class of this embodiment, the curve-fitting calculation is conducted on the second-order Raman spectra using a Gaussian curve fitting calculating method, and a number of peaks is eight.

In a class of this embodiment, in (1), the Raman spectral characteristic parameters of standard coals comprise at least one of the following parameters: peak areas $I_{2670}$, $I_{2810}$, $I_{3060}$, and $I_{3180}$ of the peak 2670 $cm^{-1}$, the peak 2810 $cm^{-1}$, the peak 3060 $cm^{-1}$, and the peak 3180 $cm^{-1}$, respectively; a total peak area $S_1$ of the first-order Raman spectra and a total peak area $S_2$ of the second-order Raman spectra, and combined parameters thereof comprising $I_{2670}/S_1$, $I_{2810}/S_1$, $I_{3060}/S_1$, $I_{2670}/S_2$, $I_{2810}/S_2$, $I_{3060}/S_2$, $I_{2670}/I_{2810}$, $I_{2670}/I_{3060}$, $I_{2670}/I_{3180}$, $I_{3180}/I_{3060}$, $I_{3180}/I_{2810}$, $I_{(2810+3060)}/I_{2670}$, and $S_2/S_1$.

The mapping relationship between the Raman spectral characteristic parameters and the characteristic parameters of the coal quality components of each standard coal, comprises a mapping relationship between the Raman spectral characteristic parameters and the characteristic parameters comprising moisture, volatile matter, fixed carbon, ash content, carbon, and hydrogen of the standard coal.

In a class of this embodiment, the mapping relationship in (1) reflects the correlation between the Raman spectral characteristic parameters and the characteristic parameters of a single coal to directly determine the coal quality in (3), or reflects the correlation between the Raman spectral characteristic parameters and the characteristic parameters of a plurality of coals to indirectly determine the coal quality in (3).

Advantages of the method for detecting coal quality using Raman spectroscopy are summarized as follows.

1. No sample preparation is involved in the test process, thus exhibiting wide applicability. All the original samples in the production process can be directly detected. The sample can be coal particles as large as centimeters, or can be pulverized coal as small as microns. In addition, the detection process is non-destructive, non-toxic and pollution-free. Therefore, it can be adapted to various coal samples in power plants, mining and other production processes.

2. The method establishes coal quality-Raman spectra relational database with sufficient data and wide applicability, thus improving the accuracy and reliability of the fast detection of coal quality.

3. The method realizes fast-quantitative analysis of coal quality. The entire detection process can be completed in a few minutes, shortening conventional detection time. In addition, the characteristic parameters associated with the coal quality components of coals are obtained using only a one-step detection, reducing the costs and improving the detection efficiency.

DETAILED DESCRIPTION OF THE EMBODIMENTS

To further illustrate the invention, experiments detailing a method for detecting coal quality based on Raman spectra analysis are described below. It should be noted that the following examples are intended to describe and not to limit the invention.

The Raman spectroscopy technique is a non-destructive test method based on the light scattering principle. When the excitation light is irradiated to a substance, the excitation light will interact with the molecules in the substance to cause the electrons to jump to the virtual state at a high energy level. The electrons in the virtual state at a high energy level will immediately jump to the low energy level due to the instability and emit light as scattered light. When the frequency of the scattered light is the same as the frequency of the incident light, the Rayleigh line is the elastic scattered light, and when the frequency of the scattered light is not equal to the frequency of the incident light, it is referred to as Raman scattering. When the frequency of the Raman scattered light is smaller than the frequency of the incident light, it is referred to as a Stokes line, and when the frequency of the scattered light is greater than the frequency of the incident light, it is referred to as an anti-Stokes line. In general, the Stokes line is symmetrically distributed with the anti-Stokes line. However, the anti-Stokes line has a relatively weak light intensity, while the Stokes line has a relatively strong light intensity mainly for Raman spectra analysis. Because Raman spectra is the change of the frequency of the scattered light caused by the interaction between the molecules in the substance and the incident light, the Raman spectra can reflect the molecular structural information inside the substance. In addition, the change of the frequency of the scattered light is expressed as Raman shift, which does not change with changes in the frequency or intensity of the incident light and is a characteristic structural parameter at the molecular level of the substance. Each substance has its own unique molecular structure, which corresponds to unique Raman spectra. Therefore, the position of the peaks in the Raman spectra and the intensity of the peaks correspond to the information on the molecular structure of the substance. The structural information at the molecular level of the substance can be revealed by analyzing the Raman spectra. This is the theoretical basis for the Raman spectra being qualitatively and quantitatively analyzed as the molecular structure of a substance.

In essence, coal is a mixture of carbon-containing macromolecules. Changes in the coal quality components will correspond to changes in the structural information at the molecular level, and the Raman spectra can detect such changes in the structural information at the molecular level well. This provides a theoretical basis for the Raman spectroscopy technology for the detection of the coal quality components.

The generation of the Raman spectra is a process of light scattering. Since light is generated and propagated at a high speed, the scattering process occurs fast, and the entire test process takes a very short time, the Raman spectra analysis provides a possibility for fast detection of coal quality.

For highly-ordered carbon material such as single-layer graphene, the Raman spectra peak is simple, and the peak intensity is large. There is graphite peak of 1580 cm$^{-1}$ (commonly referred to as G peak) corresponding to the vibration mode of the graphite molecule $2E_{2g}$. A 2D peak appears near 2670 cm$^{-1}$. In the embodiment of the disclosure, the Raman spectra of the carbon material in the range of 600-3400 cm$^{-1}$ is divided into a first-order Raman spectra of 600-2200 cm$^{-1}$ and a second-order of 2200-3400 cm$^{-1}$ according to the Raman spectra range. In general, the second-order Raman spectra is the frequency-doubling and sum-frequency peak of the first-order Raman spectra, and has peak intensity weaker than that of the first-order Raman spectra.

With the increase of defects in graphite crystals, there will be defect peaks of 1350 cm$^{-1}$ (commonly referred to as D peak), 1610 cm$^{-1}$ (commonly referred to as D' peak), 1450 cm$^{-1}$ (commonly referred to as V peak), 2900 cm$^{-1}$ (commonly referred to as D+G peak), and 3180 cm$^{-1}$ (commonly referred to as 2G peak) in the Raman spectra. With the presence of H, O and other heterocyclic atoms, there will be peaks of 1230 cm$^{-1}$ (commonly referred to as S peak), 2500 cm$^{-1}$ (commonly referred to as 2S peak), 3060 cm$^{-1}$ (commonly referred to as $2V_L$ peak), and 2800 cm$^{-1}$ (commonly referred to as $2V_R$ peak). The $2V_L$ peak is more sensitive to the C—H structure content and the small-ring molecules in the carbon structure, while the S peak and 2S peak are more sensitive to the change of the oxygen-containing functional group in the carbon structure.

For highly-disordered carbon material such as coal, coal coke, and coke, there are many peaks in the Raman spectra because of more defects and heterocyclic atoms, and there is a superposition between the peaks. Therefore, the peak deconvolution needs to be performed on the corresponding Raman spectra so as to obtain more detailed Raman spectral characteristic parameters.

Based on the above principle, the main technical solution proposed by the disclosure is as follows:

(1) establishing coal quality-Raman spectra relational database selecting a plurality of standard coals of different coal ranks and different ash contents, acquiring Raman spectral characteristic parameters of each standard coal and characteristic parameters of coal quality components of each standard coal, calculating a mapping relationship between the Raman spectral characteristic parameters and the characteristic parameters of the coal quality components of each standard coal, to establish a relational database of the Raman spectral characteristic parameters and the characteristic parameters of the coal quality components;

(2) providing coal to be analyzed, conducting a Raman spectroscopy on the coal following operations in (1), to yield Raman spectrum of the coal, and performing curve-fitting calculation on the Raman spectrum of the coal, to obtain Raman spectral characteristic parameters of the coal; and (3) comparing the Raman spectral characteristic parameters of the coal with the Raman spectral characteristic parameters of the relational database, and based on the mapping relationship between the Raman spectral characteristic parameters and the characteristic parameters of the coal quality components obtained in 1), determining coal quality of the coal.

One embodiment of the disclosure and an application example based on the embodiment are described below.

(1) Coal quality-Raman spectra relational database is established: a plurality of standard coals of different coal ranks and different ash contents are selected, and the Raman spectroscopy, industrial analysis, and elemental analysis are performed on standard coals, respectively.

(1a) The Raman spectral characteristic parameters of coal are obtained by the Raman spectroscopy, comprising: the peak areas of the wave peaks of 2670 cm$^{-1}$, 2810 cm$^{-1}$, 3060 cm$^{-1}$, and 3180 cm$^{-1}$ contained in the Raman spectra in the range of 600-3400 cm$^{-1}$ which are $I_{2670}$, $I_{2810}$, $I_{3060}$, and $I_{3180}$, respectively, the total peak areas $S_1$ and $S_2$ of the first-order Raman spectra and the second-order Raman spectra, and their combinations $I_{2670}/S_1$, $I_{2810}/S_1$, $I_{3060}/S_1$, $I_{2670}/S_2$, $I_{2810}/S_2$, $I_{3060}/S_2$, $I_{2670}/I_{2810}$, $I_{2670}/I_{3060}$, $I_{2670}/I_{3180}$, $I_{3180}/I_{3060}$, $I_{3180}/I_{2810}$, $I_{(2810+3060)}/I_{12670}$, $S_2/S_1$, etc., and other similar correlated combinations, wherein $I_{(2810+3060)}$ represents the sum of $I_{2810}$ and $I_{3060}$.

In the calculation process of the above parameters, the Raman spectra needs to be preprocessed. The preprocessing comprises a Raman spectra segmentation process, which is divided into a first-order Raman spectra and a second-order Raman spectra. A baseline removing process is performed on the first-order Raman spectra and the second-order Raman spectra, respectively. The total peak area $S_1$ of the first-order Raman spectra is calculated, and curve-fitting calculation is conducted on the second-order Raman spectra to obtain the total peak area $S_2$ of the second-order Raman spectra. Curve-fitting calculation is conducted on the second-order Raman spectra using a Gaussian curve fitting calculating method. In this embodiment, the number of peaks is eight, and in other embodiments, other numbers of peaks may be further comprised for calculation.

When the Raman spectrum of standard coals is preprocessed, the smoothing process is not performed as much as possible to prevent the distortion of the spectrum in the smoothing process from resulting in changes in the relevant characteristic parameters in the spectrogram. When the curve-fitting calculation is conducted on the Raman second-order spectrogram, the curve-fitting calculation is conducted mainly based on the eight peaks shown in FIG. 4.

(1b) The characteristic parameters of different coal quality components such as the respective moisture (M), volatile matter (V), fixed carbon (FC), ash content (A), carbon (C), hydrogen (H), etc., in different standard coals are obtained through industrial analysis and elemental analysis, such as its independent content (%), or the correlated amount (such as the ratio C/H of C to H in coals).

As a further preferred solution, the standard coals selected in the database establishing process of this embodiment are non-mixed coals and cover a plurality of coals of different coal ranks and different ash contents. It is preferred to select unmixed raw ore coals and to select as many types of coals as possible to ensure the comprehensiveness and wide applicability of the database. In the database establishing process, the coal quality components of standard coals are obtained from industrial analysis and elemental analysis according to Chinese national standard GB/T212-2008 and GB476-91, and the same base is used for different standard coals. Both air dry base and dry base can be used.

(1c) The relationship between characteristic parameters of each Raman spectra in (1a) and different characteristic parameters of each coal quality component in (1b) is calculated, respectively, to obtain its mapping relationship. The relational database between the Raman spectral characteristic parameters and the coal quality component characteristic parameters of coals is established (coal quality-Raman spectra relational database). More specifically, the coal quality component characteristic parameters may be taken as the abscissa and the Raman spectral characteristic parameters may be taken as the ordinate, respectively, to draw a curve graph of the mapping relationship therebetween. In the actual test, a Raman spectral parameter may reflect a plurality of coal quality components correspondingly, or a plurality of Raman spectral parameters may reflect the same coal quality component correspondingly. Therefore, the Raman spectral characteristic parameters finally selected to establish the coal quality-Raman spectra relational database may be one or more parameters in (1a). According to the method provided by the disclosure, the more Raman spectral characteristic parameters are selected in the coal quality-Raman spectra relational database, the more established mapping relationships between the coal Raman spectral characteristic parameters and the coal quality component characteristic parameters, and the wider the scope of application of detection of the coal quality-Raman spectra relational database there will be.

When the mapping relationship between the coal quality and Raman spectral characteristic parameters is established, as many as possible Raman spectral characteristic parameters that can better reflect the coal quality components are selected. In this way, the comparing calculation is performed according to the obtained relevant Raman spectral characteristic parameters of the coals to be detected and the established coal quality-Raman spectra relational database, so that the various coal quality components of the coals to be detected can be directly or indirectly obtained.

(2) The process for fast detecting coal quality is as follows: conducting the Raman spectroscopy on the coal following the operations in (1), preprocessing the detected Raman spectra, and performing curve-fitting calculation on the Raman spectrum to obtain the relevant Raman spectral characteristic parameters of the coal.

(3) Comparing and matching with the established coal quality-Raman spectra relational database, and obtaining the coal quality component characteristic parameters of M, V, FC, A, C, H, etc., of the coal according to the mapping relationship between the relevant Raman spectral characteristic parameters and the coal quality components in the database.

An application example based on the embodiment is as follows.

1) 50 standard coals of different coal ranks and different ash contents are selected, ground to 74-105 μm, and numbered as 1-50. Industrial analysis and elemental analysis are conducted, respectively. As a result, air dry base is used. For the sake of simplicity, only the relevant data of the typical 10 standard coals are listed here, as shown in Table 1.

TABLE 1

| No. | Moisture (M, %) | Volatile matter (V, %) | Fixed carbon (FC, %) | Ash content (A, %) | C (%) | H (%) | N (%) | S (%) |
|---|---|---|---|---|---|---|---|---|
| 1 | 14.34 | 24.91 | 53.91 | 6.84 | 61.45 | 4.29 | 0.45 | 0.41 |
| 2 | 1.83 | 7.54 | 67.49 | 23.14 | 62.24 | 4.20 | 0.46 | 0.68 |
| 3 | 3.07 | 28.92 | 51.39 | 16.61 | 68.76 | 4.22 | 1.03 | 0.67 |
| 4 | 1.28 | 4.85 | 62.02 | 31.85 | 56.95 | 1.95 | 0.75 | 0.50 |
| 5 | 8.78 | 32.25 | 54.37 | 4.60 | 67.71 | 4.64 | 0.81 | 0.39 |
| 6 | 12.47 | 25.78 | 57.11 | 4.64 | 63.00 | 4.09 | 0.66 | 0.67 |
| 7 | 1.75 | 9.72 | 68.13 | 20.40 | 73.93 | 3.19 | 1.19 | 0.64 |
| 8 | 1.50 | 22.74 | 47.40 | 28.35 | 43.60 | 2.84 | 0.67 | 4.01 |
| 9 | 22.10 | 34.93 | 35.47 | 7.50 | 63.11 | 6.11 | 1.69 | 3.23 |
| 10 | 1.62 | 19.05 | 48.88 | 30.45 | 67.68 | 2.50 | 0.89 | 0.71 |

2) The Raman test is conducted on 50 standard coals samples, respectively. Raman spectra of the samples can be obtained in a micro-Raman spectrometer (RAM HR800). The Raman test conditions are as shown in Table 2.

TABLE 2

| Laser wavelength | Laser power | Eyepiece multiplier | Scanning time | Scanning range |
|---|---|---|---|---|
| 532.16 nm | 5 mw | ×50 | 15 s | 600-3400 cm$^{-1}$ |

Figure 1:
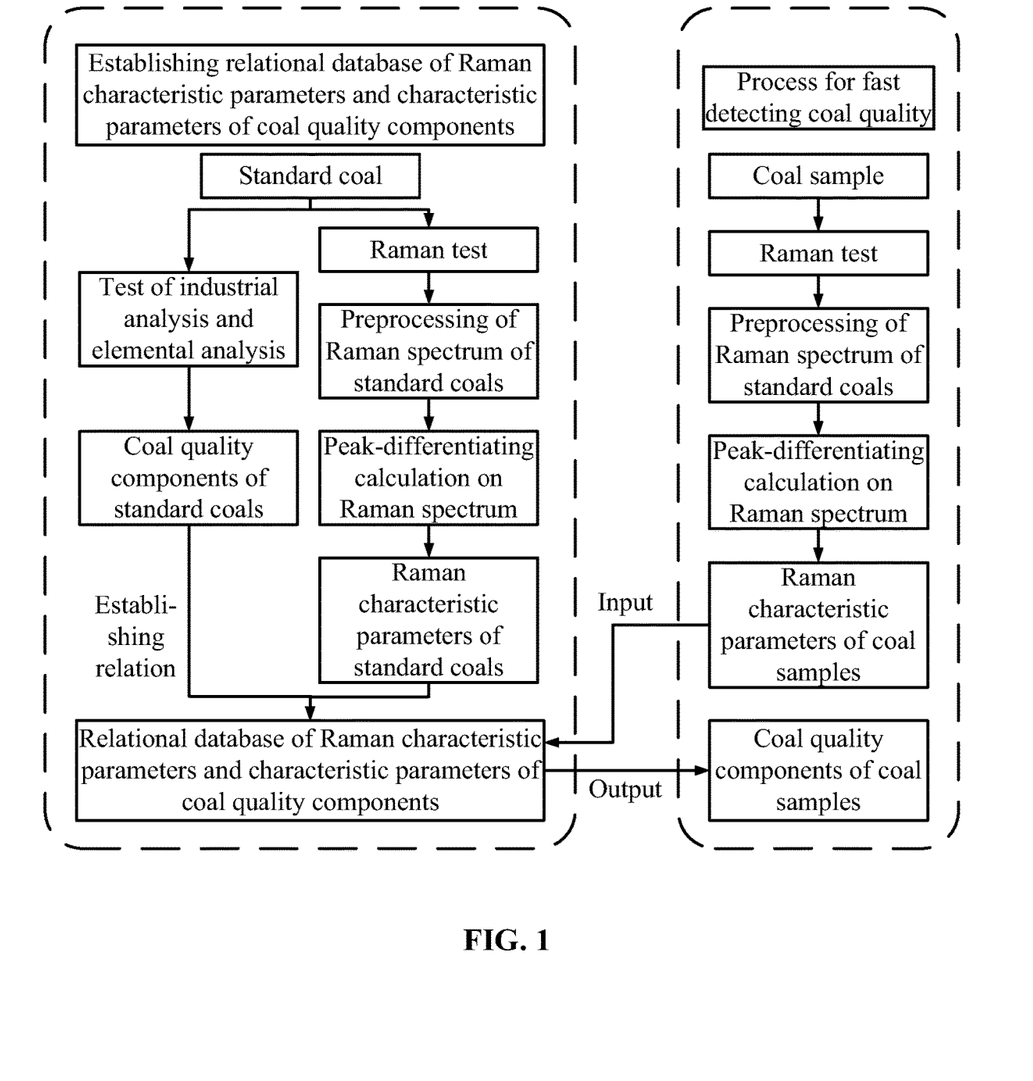
FIG. 1 is a flowchart of a method for detecting coal quality according to one embodiment of the disclosure.
Figure 2:
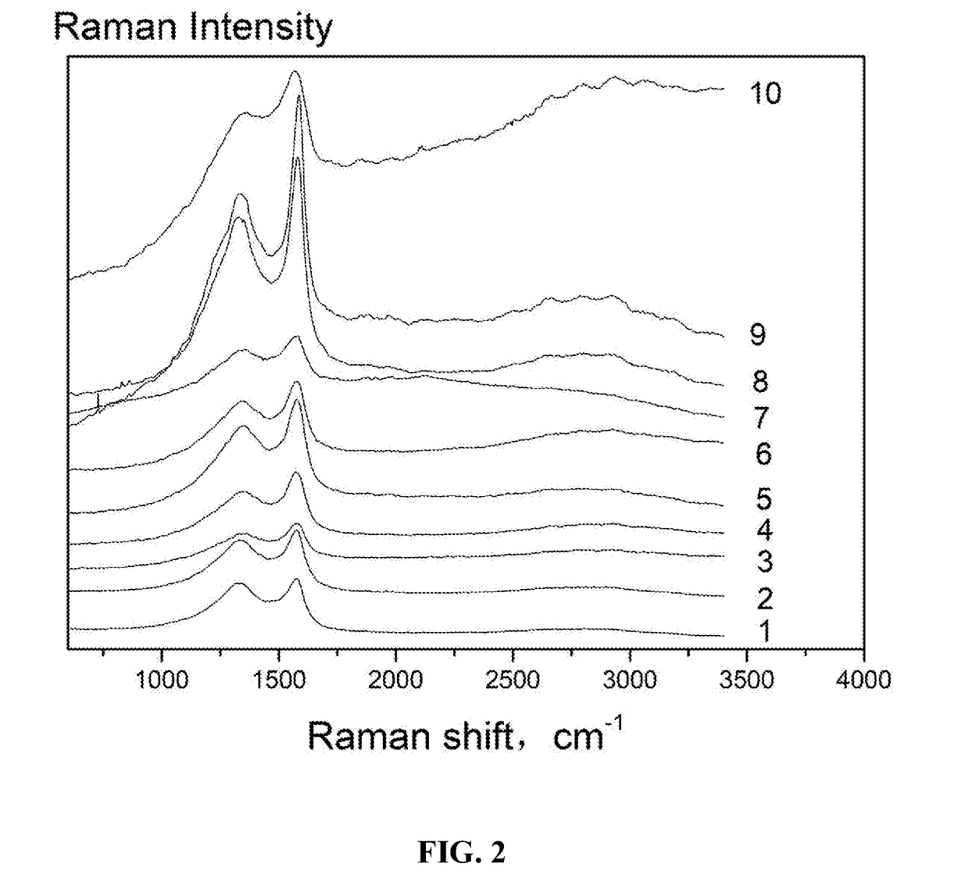
FIG. 2 illustrates Raman spectra of ten typical standard coals.
Figure 3A:
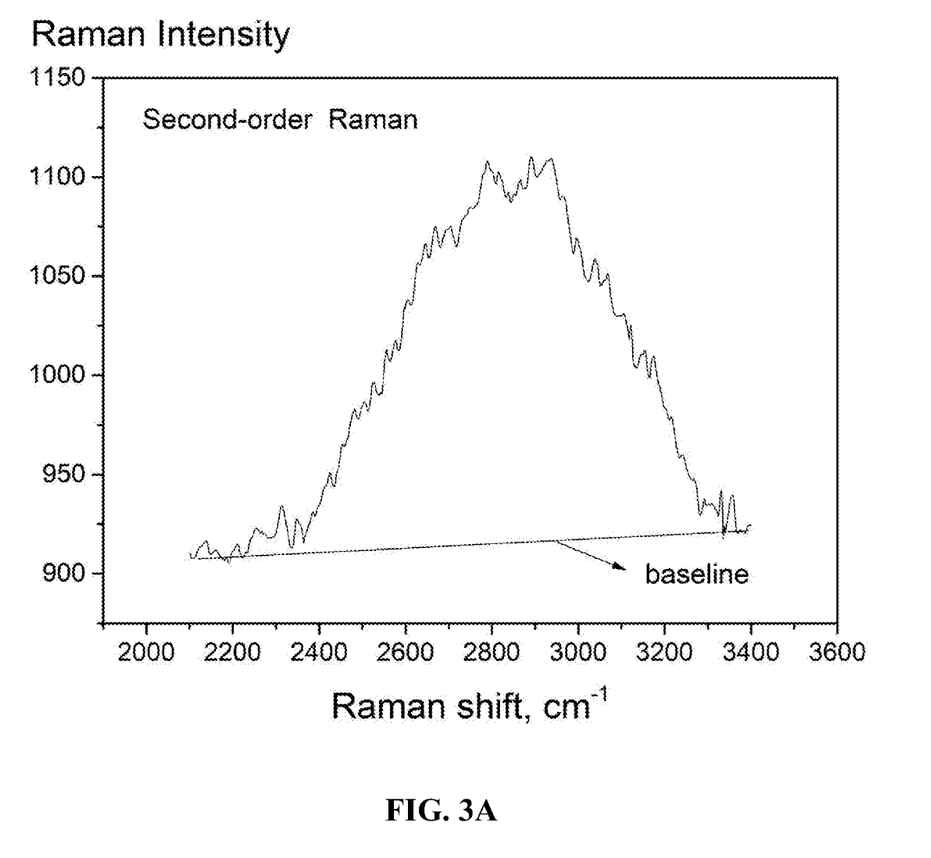
FIG. 3A shows a baseline correction of a first-order Raman spectra baseline.
Figure 3B:
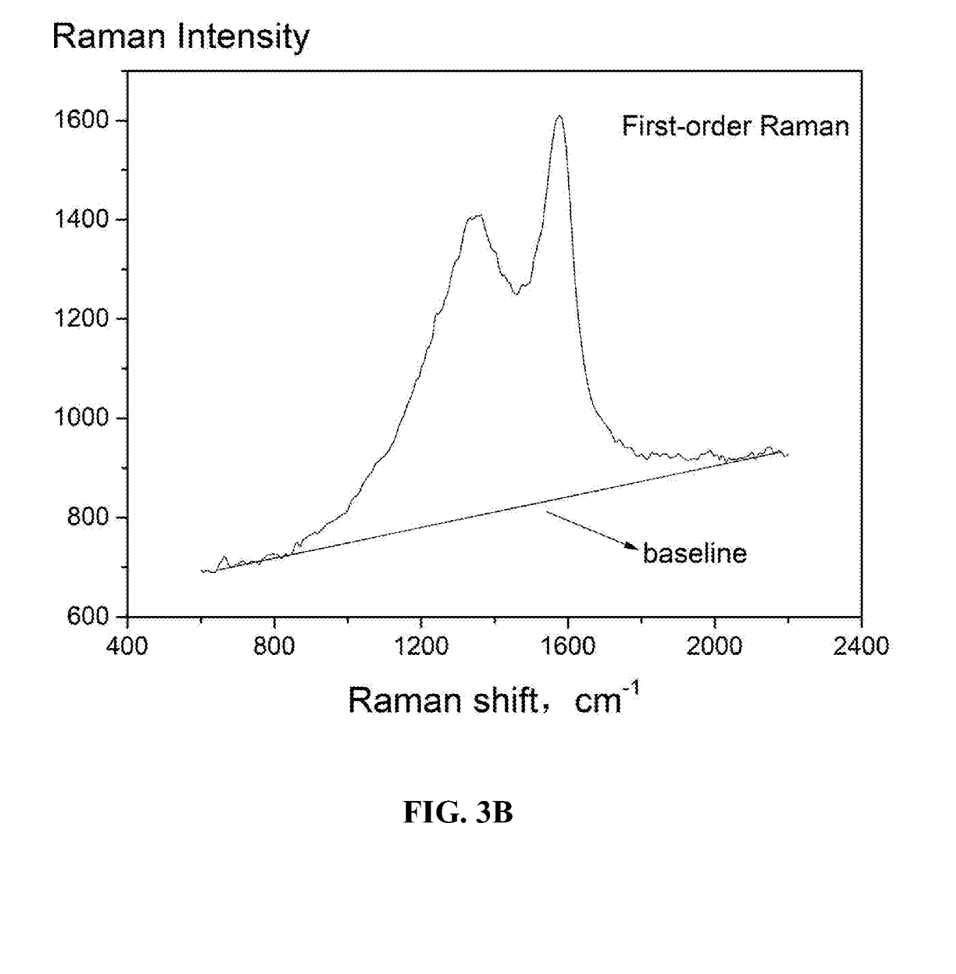
FIG. 3B is shows a baseline correction of a second-order Raman spectra baseline.

3) The obtained Raman spectra of typical 10 coals is as shown in FIG. 2. It can be seen from the figure that there is a partial baseline drift in the Raman spectrogram of the coals. In order to more accurately obtain the Raman spectral characteristic parameters, the Raman spectra is divided into a first-order Raman spectra of 600-2200 cm$^{-1}$ and a second-order Raman spectra of 2200-3400 cm$^{-1}$ and the baseline correction is performed. The baseline correction method is a two-point straight line method, as shown in FIGS. 3A-3B.

Figure 4:
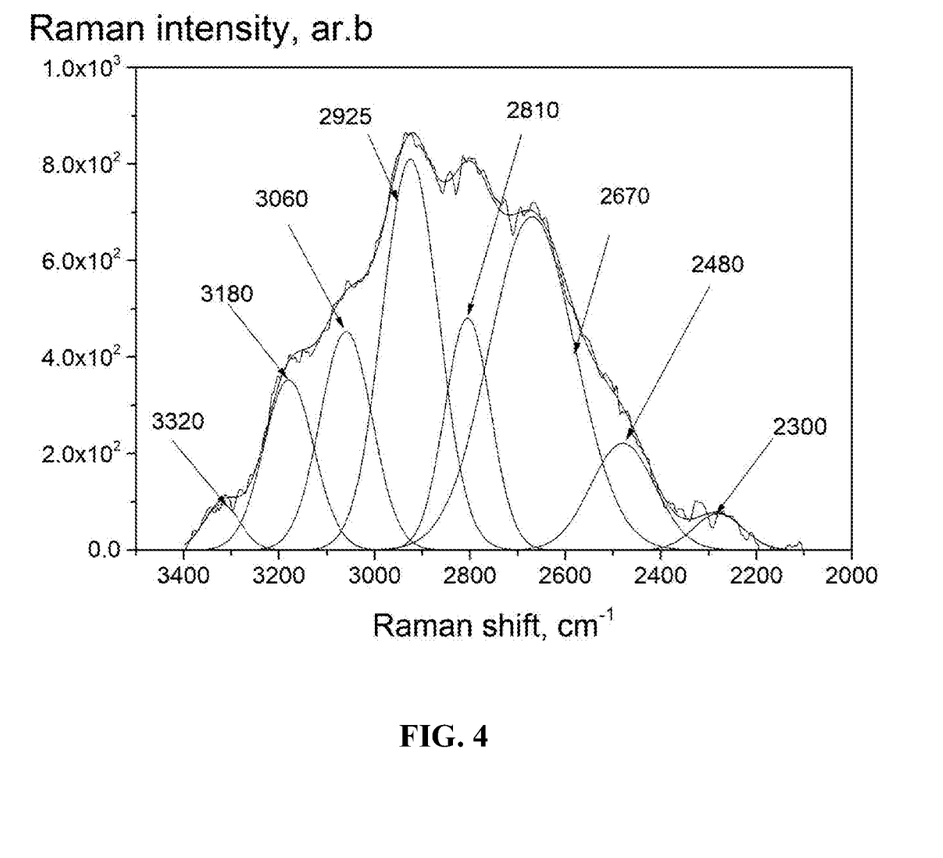
FIG. 4 is a separation diagram of a second-order Raman spectra according to one embodiment of the disclosure.

4) Due to the existence of a plurality of peaks in the Raman spectra of coal which is a highly-disordered carbon material and due to a superposition between the peaks, in order to obtain the Raman spectra relevant characteristic parameters as much and accurately as possible, the curve-fitting process is performed on the second-order Raman spectra of the coal. An example of curve-fitting is as shown in FIG. 4. The area of each peak and its combination is calculated after the curve-fitting, comprising: the relevant Raman spectral characteristic parameters such as $I_{2670}$, $I_{2810}$, $I_{3060}$, $I_{3180}$, $S_1$, $S_2$, $I_{2670}/S_1$, $I_{2810}/S_1$, $I_{3060}/S_1$, $I_{2670}/S_2$, $I_{2810}/S_2$, $I_{3060}/S_2$, $I_{2670}/I_{2810}$, $I_{2670}/I_{3060}$, $I_{2670}/I_{3180}$, $I_{3180}/I_{3060}$, $I_{3180}/I_{2810}$, $I_{(2810+3060)}/I_{2670}$, etc.

Figure 5:
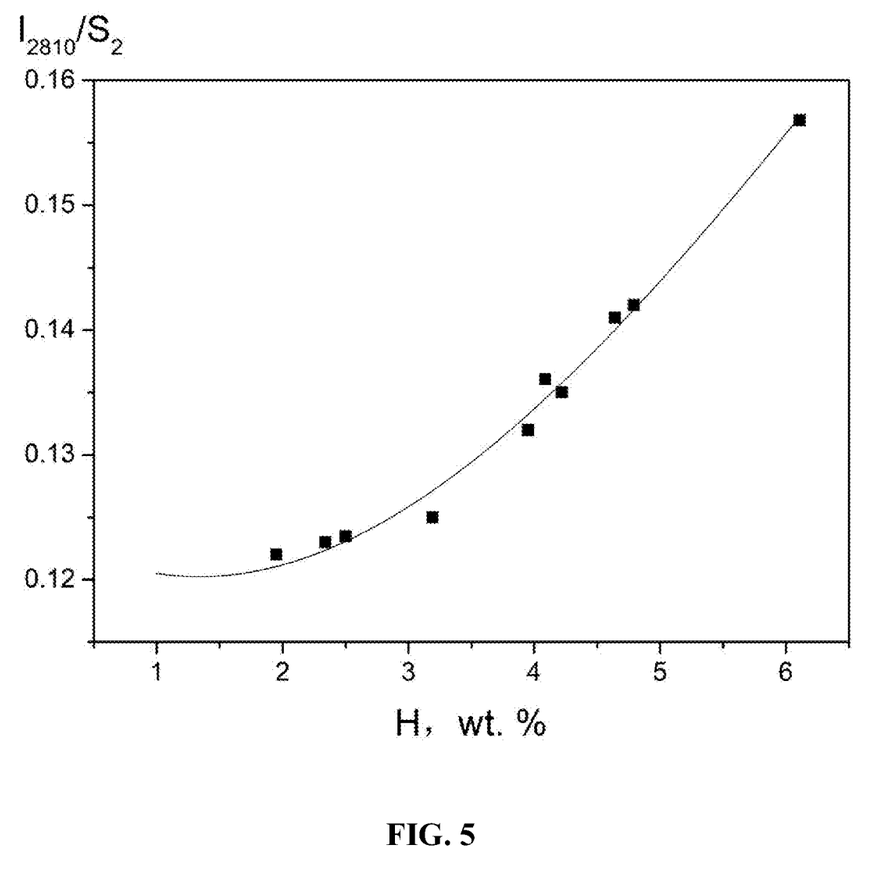
FIG. 5 shows a mapping relationship between Raman spectra characteristic parameter $I_{(2810+3060)}/I_{2670}$ and H content in a coal.

5) The relevant Raman spectral characteristic parameters calculated after the curve-fitting and the coal quality component characteristic parameters obtained by the industrial analysis and elemental analysis of standard coals are mapped and correlated so as to establish coal quality-Raman spectra relational database. In this specific application example, a mapping relationship established between one of the Raman spectral characteristic parameters $I_{(2810+3060)}/I_{2670}$ and the coal quality hydrogen (H) content is taken as an example. The mapping relationship is as shown in FIG. 5.

6) According to the process from step 2) to step 4), the Raman test is conducted on the coal using the same manner and base. The relevant Raman spectral characteristic parameters of the coal which are obtained by calculation are as shown in Table 3. In Table 3, the unit of $I_{2670}$, $I_{2810}$, $I_{3060}$, $I_{3180}$, $S_1$, and $S_2$ is arb. unit, i.e., an arbitrary unit. Since the peak intensity has no definite physical unit and is only the signal intensity, the area has no determined unit either. The detection and calculation can be performed only using the same size and base.

TABLE 3

Raman spectral characteristic parameters of to-be-detected coal

| | |
|---|---|
| $I_{2670}$ | 22400.69 |
| $I_{2810}$ | 12154.65 |
| $I_{3060}$ | 12253.18 |
| $I_{3180}$ | 10121.41 |
| $S_1$ | 359175.70 |
| $S_2$ | 89570.00 |
| $I_{2670}/S_1$ | 0.06 |
| $I_{2670}/S_2$ | 0.25 |
| $I_{2810}/S_1$ | 0.03 |
| $I_{2810}/S_2$ | 0.14 |
| $I_{3060}/S_1$ | 0.03 |
| $I_{3060}/S_2$ | 0.14 |
| $I_{3180}/S_1$ | 0.03 |
| $I_{3180}/S_2$ | 0.11 |
| $I_{2670}/I_{2810}$ | 1.84 |
| $I_{2670}/I_{3060}$ | 1.83 |
| $I_{2670}/I_{3180}$ | 2.21 |
| $I_{3180}/I_{3060}$ | 0.83 |
| $I_{3180}/I_{2810}$ | 0.83 |
| $I_{(2810+3060)}/I_{2670}$ | 0.96 |

7) The relevant Raman spectral characteristic parameters of the coal, which are obtained by calculation are input into the coal quality-Raman spectra relational database.

In this application example, hydrogen content in the coals to be detected can be calculated from the mapping relationship between the Raman spectral characteristic parameters $I_{(2810+3060)}/I_{2670}$ and the coal quality hydrogen (H) content in the coal quality-Raman spectra relational database, and so on. The value of C/H can also be obtained according to the mapping relationship between the Raman spectral characteristic parameters and C/H in the coal quality-Raman spectra relational database so as to calculate the C content. By analogy, applying the method for the disclosure can directly or indirectly calculate the coal quality components such as moisture (M), volatile matter (V), fixed carbon (FC), ash content (A), C, H, etc., in the coals to be detected. The final detected content of the above coal quality components in this application example is as shown in Table 4.

TABLE 4

| Coal quality parameters of coal to be detected (Air dried basis) | |
|---|---|
| Moisture (M, wt. %) | 7.98 |
| Volatile matter (V, wt. %) | 29.58 |
| Fixed carbon (FC, wt. %) | 45.49 |
| Ash content (A, wt. %) | 16.95 |
| C (wt. %) | 62.58 |
| H (wt. %) | 4.24 |

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for detecting coal quality of coal, the method comprising:
   (1) selecting a plurality of standard coals with different coal ranks and different ash contents, acquiring Raman spectral characteristic parameters of each standard coal, acquiring characteristic parameters of coal quality components of each standard coal through elemental analysis, calculating a mapping relationship between the Raman spectral characteristic parameters and the characteristic parameters of coal quality components of each standard coal, to establish a relational database of the Raman spectral characteristic parameters and the characteristic parameters of coal quality components;
   (2) providing a coal sample to be analyzed, conducting a Raman spectroscopy on the coal sample to yield a Raman spectrum of the coal sample, and performing curve-fitting calculation on the Raman spectrum of the coal sample to obtain Raman spectral characteristic parameters of the coal sample; and
   (3) comparing the Raman spectral characteristic parameters of the coal sample with the Raman spectral characteristic parameters of the relational database, and based on the mapping relationship between the Raman spectral characteristic parameters and the characteristic parameters of coal quality components obtained in (1), determining the coal quality of the coal sample;
   wherein:
      in (1), the Raman spectral characteristic parameters of standard coals comprise at least one of the following parameters: peak areas $I_{2670}$, $I_{2810}$, $I_{3060}$, and $I_{3180}$ of the wave peak 2670 $cm^{-1}$, the wave peak 2810 $cm^{-1}$, the wave peak 3060 $cm^{-1}$, and the wave peak 3180 $cm^{-1}$, respectively; a total peak area $S_1$ of the first-order Raman spectra and a total peak area $S_2$ of the second-order Raman spectra, and combined parameters thereof comprising $I_{2670}/S_1$, $I_{2810}/S_1$, $I_{3060}/S_1$, $I_{2670}/S_2$, $I_{2810}/S_2$, $I_{3060}/S_2$, $I_{2670}/I_{2810}$, $I_{2670}/I_{3060}$, $I_{2670}/I_{3180}$, $I_{3180}/I_{3060}$, $I_{3180}/I_{2810}$, $I_{(2810+3060)}/I_{2670}$, and $S_2/S_1$; and
      the characteristic parameters of coal quality components comprise moisture content, volatile matter content, fixed carbon content, ash content, carbon content, and hydrogen content, and correlated ratios thereof.

2. The method for claim 1, wherein the plurality of standard coals are raw ore coals and each standard coal is a representative coal type.

3. The method for claim 1, wherein the Raman spectra is spectra are preprocessed in (1) by segmenting each of the Raman spectra into a first-order Raman spectrum and a second-order Raman spectrum, and then removing baselines of the first-order Raman spectrum and the second-order Raman spectrum.

4. The method for claim 3, wherein a detection range of the Raman spectra is between 600 and 3400 $cm^{-1}$, with 600-2200 $cm^{-1}$ as the first-order Raman spectra and 2200-3400 $cm^{-1}$ as the second-order Raman spectra.

5. The method for claim 4, wherein in (2), a total peak area of the first-order Raman spectra is calculated, and the curve-fitting calculation is conducted on the second-order Raman spectra.

6. The method for claim 5, wherein the curve-fitting calculation is conducted on the second-order Raman spectra using a Gaussian curve fitting calculating method, and a number of peaks is eight.

7. The method for claim 1, wherein the mapping relationship in (1) reflects a correlation between the Raman spectral characteristic parameters and the characteristic parameters of a single coal to directly determine the coal quality, or reflects a correlation between the Raman spectral characteristic parameters and the characteristic parameters of a plurality of coals to indirectly determine the coal quality.

* * * * *